(12) United States Patent
Huber et al.

(10) Patent No.: US 12,380,975 B2
(45) Date of Patent: Aug. 5, 2025

(54) HOLISTIC APPROACH FOR CREATING STRUCTURED MEDICAL FINDINGS REPORT

(71) Applicant: Smart Reporting GmbH, Munich (DE)

(72) Inventors: Thomas Huber, Munich (DE); Martin Schulze, Munich (DE); Sigrid Auweter, Puchheim (DE); Wieland Sommer, Munich (DE); Vlad Lazar, Munich (DE)

(73) Assignee: SMART REPORTING GMBH, Munich (DE)

( * ) Notice: Subject to any disclaimer, the term of this patent is extended or adjusted under 35 U.S.C. 154(b) by 243 days.

(21) Appl. No.: 18/266,452

(22) PCT Filed: Dec. 15, 2020

(86) PCT No.: PCT/EP2020/086162
§ 371 (c)(1),
(2) Date: Jun. 9, 2023

(87) PCT Pub. No.: WO2022/128070
PCT Pub. Date: Jun. 23, 2022

(65) Prior Publication Data
US 2024/0047029 A1 Feb. 8, 2024

(51) Int. Cl.
*G16H 15/00* (2018.01)
(52) U.S. Cl.
CPC .................................. *G16H 15/00* (2018.01)

(58) Field of Classification Search
CPC ........ G06F 40/166; G06F 30/13; G06F 30/27; G06F 9/44; G06F 30/12; G06F 30/18;
(Continued)

(56) References Cited

U.S. PATENT DOCUMENTS

| | | |
|---|---|---|
| 7,155,447 B2 | 12/2006 | Roberge et al. |
| 9,043,206 B2 | 5/2015 | Roberge et al. |

(Continued)

OTHER PUBLICATIONS

International Search Report and Written Opinion for International Application No. PCT/EP2020/086162 dated Sep. 14, 2021 (15 pages).

*Primary Examiner* — Rayeez R Chowdhury
(74) *Attorney, Agent, or Firm* — QUARLES & BRADY LLP

(57) ABSTRACT

A method, a computer system, and a computer program product for creating medical findings reports are introduced. Using these, hierarchically organized and dynamically adaptable data structure and a text editing interface are provided. A report text consisting of user-entered free text and/or structured text, that is stored in the data structure elements and transferred into the report text, is created. In the report text, first report text elements, that can be assigned to at least one data structure element, and second report text elements, that cannot be assigned to any of the existing data structure elements, are identified. The first report text elements are then assigned to the at least one data structure element. The second report text elements are then assigned and stored to one or more newly created data structure elements and/or to existing data structure elements while maintaining the order of the report text.

20 Claims, 6 Drawing Sheets

(58) Field of Classification Search
CPC .......... G06F 30/20; G06F 3/0484; G06F 8/33; G06F 17/00; G06F 17/10; G06F 3/00; G06F 40/14
See application file for complete search history.

(56) References Cited

U.S. PATENT DOCUMENTS

| | | | |
|---|---|---|---|
| 2010/0057685 A1* | 3/2010 | Luhn | G06F 16/313 707/E17.014 |
| 2014/0052444 A1* | 2/2014 | Roberge | G10L 15/08 704/243 |
| 2015/0033111 A1 | 1/2015 | Sevenster et al. | |

* cited by examiner

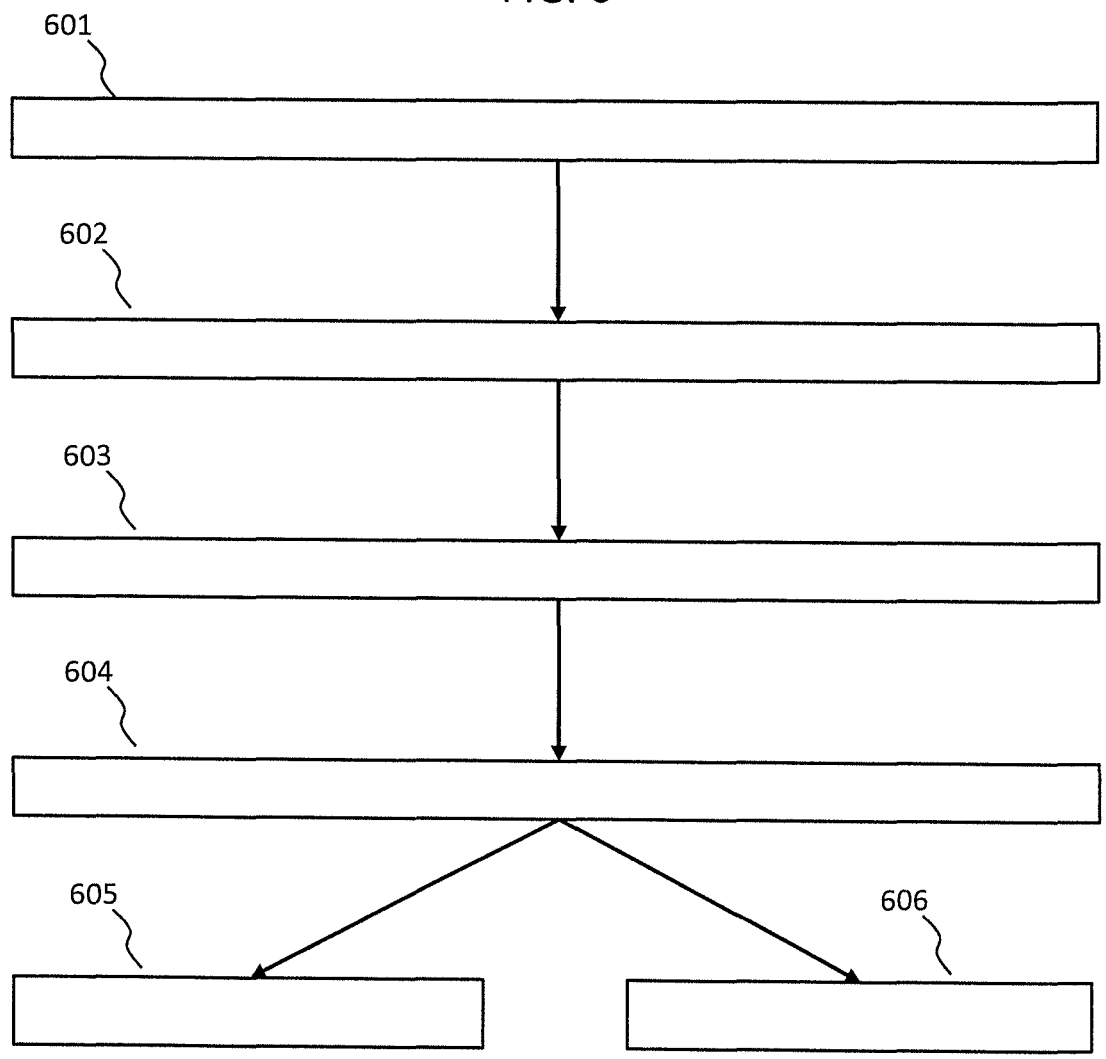

HOLISTIC APPROACH FOR CREATING STRUCTURED MEDICAL FINDINGS REPORT

CROSS-REFERENCE TO RELATED APPLICATIONS

This application is a United States national phase application under U.S.C. § 371 of International Patent Application No. PCT/EP2020/086162, filed Dec. 15, 2020, and now published as WO 2022/128070, which designates the United States. The disclosure of this international patent application is incorporated by reference herein for all purposes.

This invention relates to the field of creating structured medical reports.

BACKGROUND OF THE INVENTION

When generating a radiological report, the reviewing radiologists summarize their observations made when reviewing medical images. In a first step, a typical radiology report is created organ by organ. E.g., in a CT of the thorax the radiologist is looking, beyond others, at the heart, pericardium, lung parenchyma and airways. In a subsequent step, the radiologist summarizes the main findings into an impression. The main findings of a report contain so-called key findings which indicate remarkable aspects found in the images.

Classically, reports are free text offering the reporting physician a high degree of flexibility. Consequently, its structure, elements, style, wording, and layout differ from physician to physician. Such reports are not machine-readable, not standardized, and not analyzable. Moreover, they are prone to artefacts and they might be ambiguous or incomplete.

To overcome the drawbacks of free-text reports, so-called structured reports were introduced. These are based on structured, machine-readable reporting templates that can be progressively filled in by radiologists leading to a standardized report. Ideally, a structured report is machine-readable, has a fixed structure and contains standardized elements, wording, and layout. In addition, pre-generated report templates can be used. These may provide case-specific structure and include recommended reporting steps.

WO 2016/135100 A1 describes an approach to provide structured reports, which proposes the use of report modules as report building blocks based on decision trees. These are based on a hierarchical tree structure that also reflects dependencies of information. The resulting medical report is then created in a modular fashion, in that medical report modules can be added step-by-step during the creation of the medical report.

To create such a structured findings report, physicians must follow the prescribed structures. This means that they can no longer proceed according to their individual habits and preferences they used to apply with free-text reports. Rather, their procedure is prescribed, in some cases, right up to the choice of concrete formulations. In extreme cases, the user only selects predefined elements, which are then combined to form a report. However, practice shows that many users find this procedure rigid, not easily usable and thus in the end inefficient. Such users therefore tend to fall back on the classic free-text reporting despite the disadvantages associated with it.

There are approaches to automatically create a structured report from a dictated audio file. U.S. Pat. No. 7,958,443 B2 describes such an approach. When dictating the report, a doctor uses predefined key words as section headings. After speech recognition, the speech recognized text is structured in two phases. In the first phase, by searching the text for the predefined key words, a computer automatically locates and marks each heading in the speech recognized text file. In the second phase, a transcriber manually locates any unmarked headings in the speech recognized text file and marks them manually. The resulting text with marked headings is then formatted either automatically or manually into a final report. However, this approach requires manual post-processing by a transcriber. In addition, more complex structures with a high degree of detail are difficult to capture.

Against this background, it is necessary to improve the generation of structured findings reports.

SUMMARY OF THE INVENTION

The invention provides a method, a system, and a computer program product to improve the generation of medical structured findings reports.

One aspect of the invention concerns a computer-implemented method for creating structured medical reports according to independent claim 1.

According to an embodiment of the invention, a hierarchically organized and dynamically adaptable data structure is provided which comprises at least one data structure element as well as a text editing interface for creating and displaying a report text consisting of user-entered free text and/or structured text stored in the data structure elements and transferred into the report text.

Furthermore, first and second report text elements contained in the report text are identified. First report text elements can be assigned to at least one data structure element and second report text elements cannot be assigned to any of the existing data structure elements. The first report text elements are then assigned to the at least one data structure element, to which they can be assigned. Further, one or more new data structure elements are created, and the second report text elements are assigned and stored to them in such a way that the order of the report text is maintained. Additionally, or alternatively, second report text elements are assigned and stored to existing data structure elements in such a way that the order of the report text created in the text editing interface is maintained.

Another aspect of the invention concerns a computer system for creating structured medical reports according to independent claim 14.

According to an embodiment if the invention, the computer system comprises a data structure providing unit configured to provide and store hierarchically organized and dynamically adaptable data structures comprising at least one data structure element.

Further, the system comprises a text editing unit configured to provide a text editing interface for creating and displaying a report text consisting of user-entered free text and/or structured text stored in the data structure elements and transferred into the report text.

Finally, the system comprises a processing unit configured to control the data structure providing unit, the text editing unit, and to identify, in the report text the first and second report text elements described above, to assign in the data structure providing unit the first report text elements to the at least one data structure element, to which they are assignable, to create in the data structure providing unit one or more new data structure elements and to store and assign in the data structure providing unit second report text elements to them in such a way that the order of the report text is maintained, and/or to assign and store in the data structure providing unit second report text elements to existing data structure elements in such a way that the order of the report text created in the text editing interface is maintained.

Another aspect of the invention concerns a computer-program product for creating structured medical reports according to independent claim 15.

The above and other advantages result from the following considerations, where aspects and embodiments of the invention are discussed and, where appropriate, reference is made to the corresponding drawings, which show preferred embodiments of the invention for illustration purposes. However, these embodiments do not necessarily represent the full scope of the invention.

BRIEF DESCRIPTION OF THE DRAWINGS

FIG. 6 schematic illustration of the steps of a method according to the invention.

DETAILED DESCRIPTION

The order of any of the steps described in the following can be changed where appropriate. Furthermore, the steps can be performed individually or in combination with each other, where appropriate.

All the method steps described above can be performed on a computer system.

According to one aspect of the invention illustrated in FIG. 6, in a step 601, a hierarchically organized and dynamically adaptable data structure comprising at least one data structure element is provided. Several different data structures may be used, and each corresponds to a template for medical findings report. The findings report templates consist of modules, which in turn are composed of findings elements. The findings elements are arranged hierarchically, i.e., there are superordinate findings elements to which one or more further findings elements can be subordinated. Depending on the findings and the degree of granularity of the report, there can be different numbers of hierarchy levels. These findings report templates are stored in the form of a hierarchical data structure, e.g., as a network or decision tree. The data structure is also dynamically adaptable. This means that it can be modified as required and, if required, at runtime. Thus, data structure elements such as leaves, entry items, objects or nodes can be created, changed, or even removed. The data structure also serves as a structural template for the respective findings report to be created.

Figure 1:
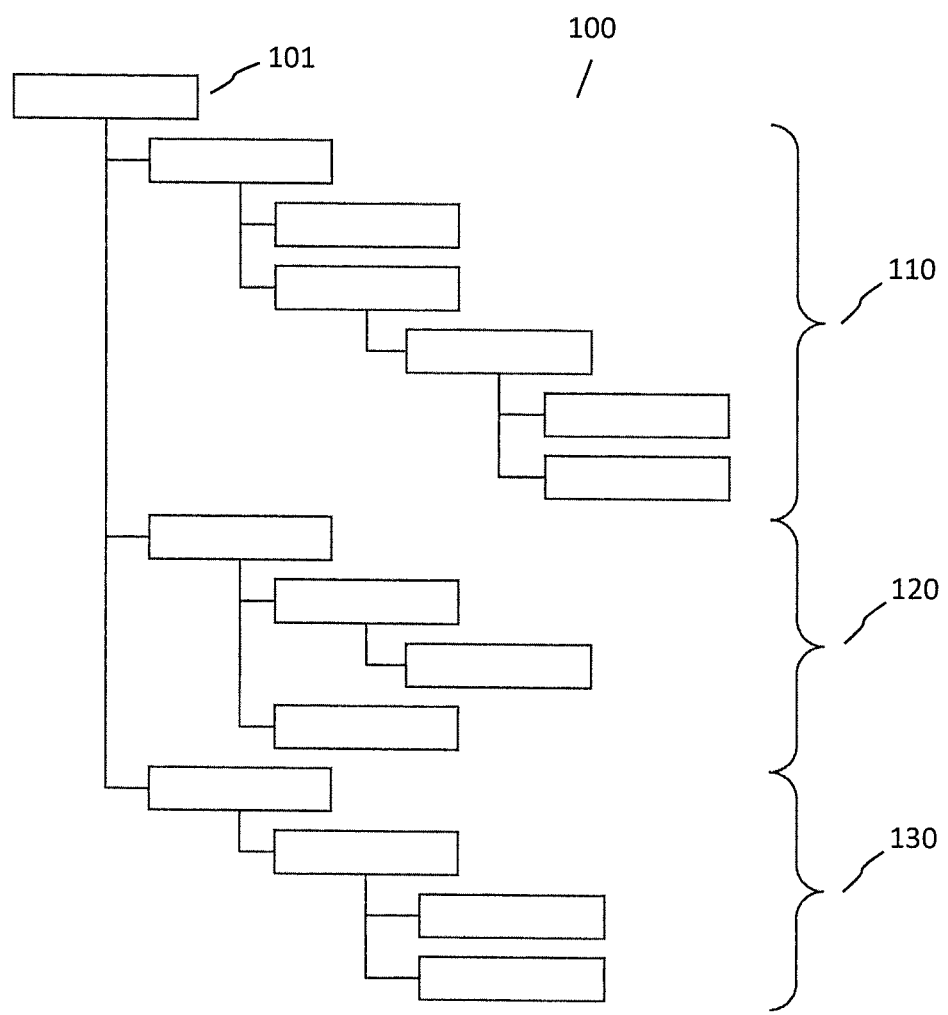
FIG. 1 schematic illustration of an example of a hierarchically ordered data structure.

FIG. 1 schematically shows a hierarchical data structure 100, which in this case is implemented as a decision tree. The data structure 100 consists of data structure elements 101, which in this example are combined to modules 110, 120 and 130. The modular design has the advantage that the data structure can be quickly extended in a modular fashion. For example, before, during or after the creation of a findings report, findings report modules that capture a specific aspect of findings can be added.

According to the same aspect, in a further step 602, a text editing interface is provided for creating a report text. The report text can be composed of user-entered free text and text that is stored in the data structure elements and transferred into the report text, e.g., by the user. The latter approach is referred to as structure-to-text mechanism.

In one embodiment, a data structure interface is provided for graphical representation and interaction with the data structure elements. For example, the user can operate the system via a user interface consisting of a findings editor and a hierarchical navigation tool (e.g., a hierarchical menu bar and/or hierarchical drop-down menus). The findings editor serves as the text editing interface and the hierarchical navigation tool as an interface to access the data structure with its modules and elements.

Figure 2:
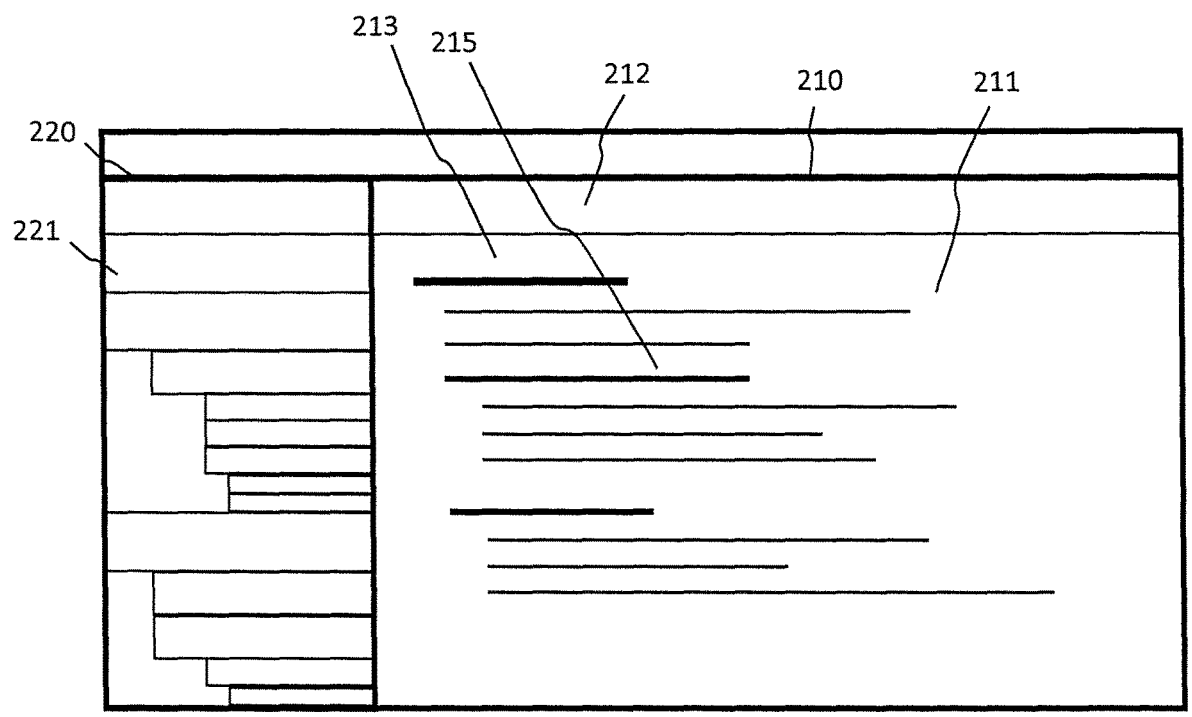
FIG. 2 schematic illustration of an example of a user interface with text editor and navigation tool.

FIG. 2 shows an example for such an arrangement. The screen is divided into text editor 210 and navigation bar 220. For example, the text editor has a text field 211 and an editing menu 212 providing text editing functions. The navigation tool 220 displays hierarchical structure elements 221 which correspond to elements of the data structure. In another example not shown, the navigation tools are displayed as an overlay in other systems, such as a picture archiving and communication system (PACS), an advanced visualization system, or any other medical IT system. In any case, only parts of the findings report template can be displayed as required, e.g., from a certain hierarchy level on or only the first element of each module, etc.

To create a medical report, the user first opens the findings editor and selects a findings report template. The user can now operate the hierarchical navigation tool 220 as well as enter free text in the text editor 210. The module-based system allows users to dynamically add further modules to the selected findings report template, or create their own findings report template by combining modules as required.

The hierarchical navigation tool 220 graphically represents the findings elements 101 of the selected findings report template and shows its hierarchy. The navigation tool can be navigated using the mouse, keyboard, voice commands, or the control keys of a dictation device. In addition, the elements of the data structure, e.g., of a decision tree, can also be read aloud (speech output). Here, modules and findings elements are accessed and selected. The selection of a module/findings element may lead to the opening and display of subordinate findings elements.

In one embodiment, text associated with data structure elements is transferred to the report text by interacting with them via the data structure interface. For example, by interacting with findings elements via the navigation tool 220 the user can cause the automatic generation of corresponding findings report texts in the editor. The generated texts correspond to text that is assigned to the respective findings element and potentially also stored there. These text entries can also be supplemented with free text in the text editor. The automatic findings texts retain the hierarchies of the findings elements and reproduce them in the text, e.g., by using headings, different fonts, and paragraphs. FIG. 2 shows an example of this. The report text is visually structured by using heading 213 and subheadings 215 that may have different fonts and/or font sizes than other parts of the text.

The findings elements selected by this process are stored as unique entries of the data structure and are available digitally to other IT applications (e.g., controlling, AI, etc.).

For better overview, the navigation element can, for example, consist of a combination of menu bar and drop-down menus. Higher hierarchical levels are displayed in the menu bar, while lower levels appear in the form of drop-down menus. The selection made in the drop-down menu can be displayed in the superordinate findings element of the menu bar.

In the text editor field, the user can enter his own, possibly unstructured, free texts at any time. The input can be made either via the keyboard or with a dictaphone and speech recognition—or an auto-text library. Users can either enter only free text or create the text as a combination of pre-defined text and free text. E.g., they can select a structural element from the menu bar and add it to the free text. Users can thus freely choose to what extent they want to use the existing structure within the scope of a free-text report. Thereby, any hierarchy level of the data structure can be adopted by the report text and, if required, be supplemented by free text. During text generation, the menu bar of the hierarchical navigation tool and the text are constantly synchronized.

In addition, the user can supplement the report text and/or the data structure with further elements. For example, hyperlinks and images can be inserted (e.g., references to medical sources, representative sample images from other medical IT systems, sketch elements created with the system, own sketch elements, etc.).

In the case of exclusive or section-wise free text input by the user, the system includes various options for achieving the greatest possible completeness, standardization, and structure in these free texts. This transfer of the free text into a given structure is also referred to as text-to-structure mechanism.

According to the above aspect of the invention, in a step 603, the system analyzes the generated report text and differentiates between first text elements which can be uniquely assigned to the data structure or at least one data structure element and second text elements which cannot be assigned to any of the existing data structure elements. Assigning or assignability of a text element means in that context that at least one data structure element already existing in the data structure corresponds to this text element. The information contained within an assignable text element is represented by one or more data structure elements and their entries in the data structure. Thus, the information can be mapped to the data structure and can be entered and stored there if required.

Text elements in this context can, e.g., be single expressions, numbers, formulae, formulations consisting of several words or entire text passages.

In case of the first (assignable) text elements, two sub-cases must be distinguished.

In the first sub-case, the first text elements have been taken from the data structure itself, i.e., using the structure-to-text mechanism described above. Such first text elements consist for example of text that has been transferred to the report text in the above-described way by the user using the navigation bar. Such first text elements are already intrinsically represented in the data structure and are already assigned to data structure elements. In this case, the text elements are already arranged following the structure defined by the data structure and assigned to the data structure elements in a trivial way when transferred to the report text.

In the second sub-case, the first text elements have been created by free text input via the text editor. Nevertheless, there are existing data structure elements already contained in the data structure that correspond to the text elements. Such text elements can, therefore, be assigned and the information contained in the text element is represented by at least one data structure element and can be entered and stored there accordingly. How to assign the text element to one or more data structure elements is not automatically clear from the beginning, i.e., during text input. However, an assignment is basically possible after text input because the information contained in the text can be represented by already existing data structure elements and their entries. This free text, initially entered without a structure, can, thus, be structured/transferred into the given structure. To identify such text elements which can be structured in principle, the system can compare, e.g., single terms, formulations consisting of several words or even whole text blocks of the freely entered text with text stored in data structure elements. Such a comparison of report text elements and text elements contained in the data structure can, e.g., be performed using continuous comparison between the free text entered by the user and the "expected" text that would have resulted from a selection of structural elements. Also, classical string comparison may be used, i.e., comparing strings in the free text with a library of strings linked to findings elements.

In one embodiment, a report text element is identified as a first report text element if by means of automatic text recognition it is determined that said report text element matches a text element stored in at least one data structure element within a predetermined linguistic similarity range. Machine learning could also be used to identify such similarities.

Such a linguistic similarity range takes into account the linguistic ambiguity and diversity, e.g., by assigning the same medical meaning to such different expressions or modes of expression It may be implemented by using different criteria for determining if two expressions match. E.g., it may be defined that a match requires a strict one-to-one match or to also cover similarities, e.g., by allowing synonyms and/or variations. This means that in addition to the specific terms or formulations, variations of them or synonyms for them can be stored in the data structure and assigned to specific findings elements.

According to the above aspect of the invention, in a step 604, the first report text elements are then assigned to their assignable at least one data structure element.

In the case of the second text elements, the system cannot assign them to existing data structure elements. No correspondence can be found in the data structure for the text elements. Thus, the information contained in the second text elements cannot be represented by the data structure.

In this case, the inventive aim is to capture such second text elements in the data structure in a manner that preserves the structure and context of the text as much as possible. The data structure must therefore offer the possibility to retain the order of the text elements as far as possible. According to the above aspect of the invention, to this end, one or more new data structure elements are created in a step 605. The second report text elements are then assigned and stored to the one or more new data structure elements in such a way that the order of the report text created in the text editing interface is maintained.

In one embodiment, this is achieved by adding second text elements as a new elements at the corresponding positions in the data structure, possibly categorized as a non-representable free text, e.g., as a new node or new leaf. To reflect the structure of the complete report text, especially the order of the text elements, as well as possible, the new data structure element must be inserted into the hierarchy as accurately as possible. If, for example, a first (assignable) text element is identified and immediately followed by one or more second (non-assignable) text elements, new data structure elements are created for these second text elements and inserted in the data structure at the hierarchy level of the first text element or at a subordinate level.

Figure 3A:
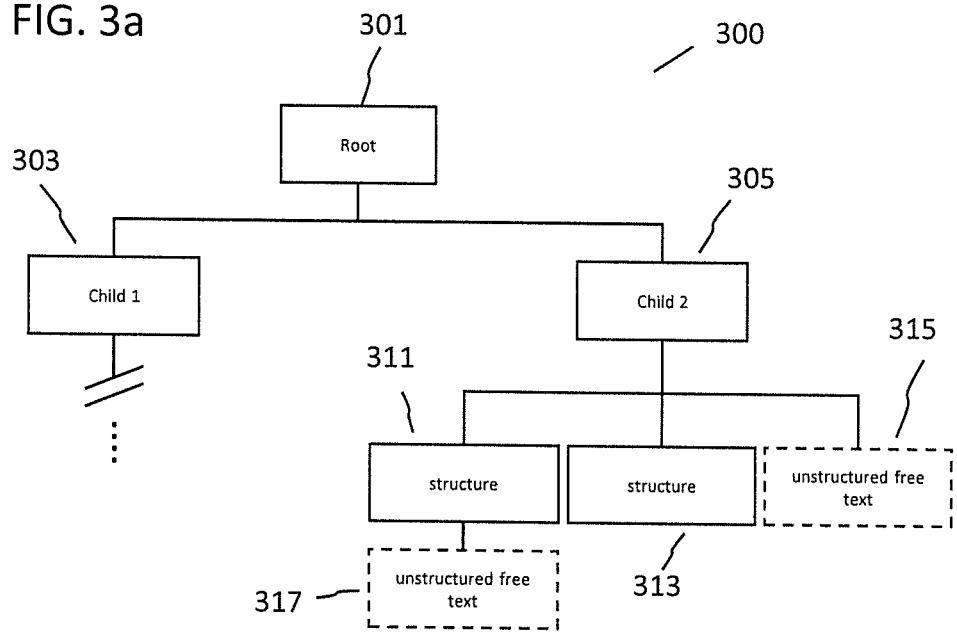
FIG. 3a schematic illustration of an example how text elements can be added as new data structure elements.

FIG. 3a illustrates an example of this. The data structure 300 has a root element 301 at the highest hierarchy level. Two children 303 and 305 branch off from this root element. Child 305 initially has two subordinate children 311 and 313, to which structured findings elements are assigned. The user now enters second text elements. This is recognized by the system and a data structure element 315 subordinate to child 305 and a data structure element 317 subordinate to child 311 is then created. The second text elements are assigned to elements 315 and 317 and their text is stored or linked there.

Additionally, or alternatively, according to the above aspect of the invention, in a step 606, the second report text elements can be assigned and stored to existing data structure elements in such a way that the order of the report text created in the text editing interface is maintained.

Figure 3B:
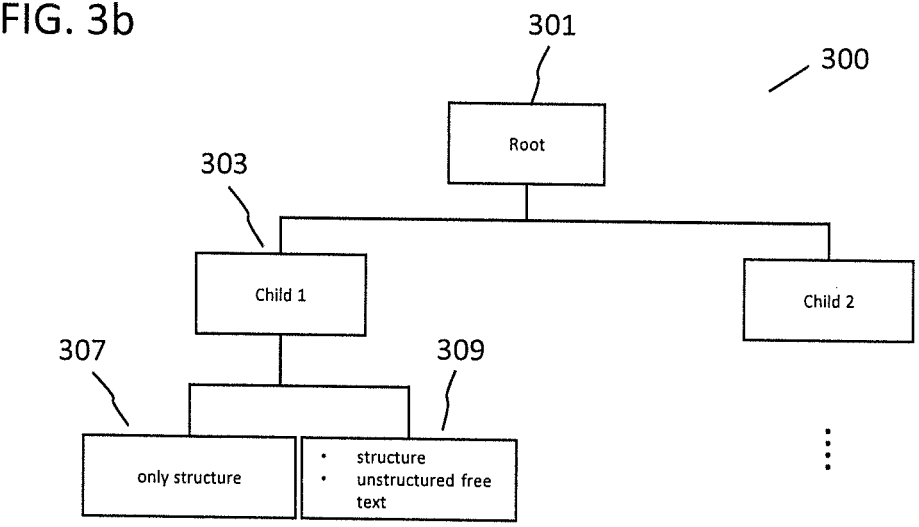
FIG. 3b schematic illustration of an example of how existing data structure elements can be extended with text elements.

In one embodiment, this is achieved by adding a non-assignable second element of the report text as an entry to an already existing data structure element. Thus, no new data structure elements are created, but existing elements are extended and/or modified. FIG. 3b illustrates this solution. Again, the top hierarchy level of the data structure 300 contains a root element 301 from which two children 303 and 305 branch off. Subordinate to child 303 are elements 307 and 309, which initially only represent structured findings report proposals and thus correspond to first text elements whose meaning can be captured by the system and represented in the data structure. Again, the user enters second, i.e., non-assignable, text elements. These are now added to data structure element 309. The element is thus extended by the second text elements and these are stored there if necessary, although the system did not recognize their meaning.

According to the invention, several approaches can be used to add freely entered text to the existing data structure. The goal is to structure both—report text elements which can be assigned to data structure elements and those which cannot be assigned according to the structure defined by the data structure used. The approaches can also be combined with each other.

Approach 1: embedding free text into its textual context. The basic idea behind this approach is that free text elements or passages remain subordinate to the hierarchical level of an already identified specific findings element and are stored accordingly in the data structure.

In a first embodiment, one or more second text elements which immediately follow a first text element are assigned to the data structure element to which the first text element is assignable, and newly created data structure elements are inserted into the data structure at the same or a subordinate hierarchy level as the data structure element to which the first text element is assignable.

In a second embodiment one or more second text elements which immediately follow a first text element are assigned and stored to the data structure element to which the first text element is assignable.

For example: in the freely entered text a text element a is recognized, which can be assigned to a data structure element A. Any free text that comes after text element a, but whose text elements cannot be assigned to any of the data structure elements, is then assigned to data structure element A until another text element 13 is identified that can be assigned to a data structure element B. For example, non-assignable free text entries under the "Aortic Valve" element in the data structure remain associated with the "aortic valve" findings element and the hierarchical structure "Findings/Aortic Valve/[free text]" until the text element "Parameters of aortic annulus (acquired in systole)" or other expected text elements in that section are identified, which can be assigned to the corresponding findings element and hierarchical structures.

Using this approach free text can, e.g., be structured in a recursive manner by iteratively segmenting the freely entered text based on first text elements that are assignable to the data structure elements at the current level of the data structure and repeating the algorithm for each text segment. Thus, segments of text are determined that are each assigned to at least one data element of the current level of the data structure. These segments may contain first and second text elements corresponding to subordinate levels of the data structure. By repeating the algorithm for each text segment, data structure level by data structure level, first and second text elements are identified, and the text is structured resp. mapped to the data structure in a recursive way.

Approach 2: providing suggestions for suitable data structure elements. During free-text reporting, the system displays suggestions for suitable findings and/or corresponding data structure elements, including associated hierarchies if necessary. This way the user is guided to apply the given structure to the report text. In one embodiment, while the report text is entered via the text editor, suggestions are made for report text elements that are contained in the data structure elements and which the user can transfer to the report text.

Figure 4:
FIG. 4 schematic representation of an example of how to use drop-down menus in the navigational toolbar.

In some embodiments, this can be implemented, for example, via a drop-down menu as shown in FIG. 4. Here the user has selected menu bar element 223 which causes drop-down menu 225 to open. Such drop-down menus could also be triggered by entered text.

These suggested findings can, e.g., be displayed to the user in the form of names of the findings elements or corresponding text suggestions and can be actively accepted or rejected by the user. Elements accepted by the user are transferred to the reports text at the position predefined by the selected report structure. Thus, these text elements appear within the reports text according to the position of the corresponding findings elements in the findings report template and are assigned to the corresponding position in the associated data structure or data structure element and saved there if necessary. In some embodiments, the selection of the displayed findings element proposals is context dependent. In particular, the respective findings report template used as well as previous findings obtained with the system affect the specific suggestions proposed.

There are several ways to determine which concrete suggestions are presented to the user. They can be used individually or in combination with each other. Their use is flexible and can be adapted by the user or the system.

1. The selection of the displayed findings element suggestions depends on the section of the findings report the user is currently working on. For example, only the findings elements that can occur in this section are displayed. In one embodiment the proposed report text elements are contained in data structure elements at the hierarchy level associated with the currently processed section of the report text.

2. Individual terms or other text elements are recognized during free text input. For example, this can be achieved by the techniques for text recognition described above. Then, findings elements that contain and/or are assigned to this term/text element are suggested to the user. The hierarchy level in which the user is currently located can also be considered. For example, in such a case, findings elements from other finding paths of higher hierarchy levels can be excluded. In one embodiment, in the case of a first text element being identified using one of the above-described text recognition techniques, it is suggested to the user to use the at least one data structure element in which the matching text element is stored for creating the report text.

3. In the system, a database of cases of other patients has been created, e.g., automatically while using the system. This database is accessed during reporting, and reporting elements that were used when reporting on similar cases as the current one are suggested to the user. In one embodiment, the suggested report text elements are contained in data structure elements that have been used in findings reports of previous, similar cases of other patients. The suggestions can be displayed in the form of descriptions of the findings elements or corresponding text suggestions. This method is also known as digital-twins method.

4. A database with cases of the same patient is created in the system, e.g., automatically while using the system. This database is accessed when the same patient is reported on again and reporting elements that have already been used for reporting on this patient are suggested to the user. For example, this could be information from preceding examinations. In one embodiment the proposed report text elements are contained in data structure elements used in previous findings reports of the same patient. Again, the suggestions can be displayed in the form of names of the findings elements or corresponding text suggestions.

5. A medical ontology is stored in the system. Based on this ontology, suggestions for renaming medical terms to the currently valid standard are displayed. For example, if the term "bronchioinvasive adenocarcinoma" is entered, the synonymous term "minimally invasive adenocarcinoma", which is currently used as the standard, is displayed.

Approach 3: Even if no suggested diagnostic elements have been selected from the hierarchical menu bar or from drop-down menus during reporting, the system still tries to make suggestions for better structuring.

If the system recognizes terms in free text that occur in the findings report template or are stored in the data structure, the user receives a suggestion as to where the text could be integrated in the findings report template. The user may be offered the possibility to accept or reject them. The free text created by the user is thus mapped to the data structure linked to the hierarchical findings report template and transferred to a (partially) structured findings report.

In one embodiment, in case of a first text element being identified using one of the techniques for recognizing text described above, it is suggested to the user to assign the identified first text element to the at least one data structure element in which the matching text element is stored.

Approach 4: The user can create his own standardized texts and/or findings templates and link them to new or existing entries in the data structure and store them there. These texts can also contain standardized gaps which can then be filled with measured values or other variable information and parameters, and which also correspond to unique entries in the data structure. In one embodiment, the user can define new data structure elements and/or text elements associated with these and transferable for the creation of a findings text.

Figure 5:
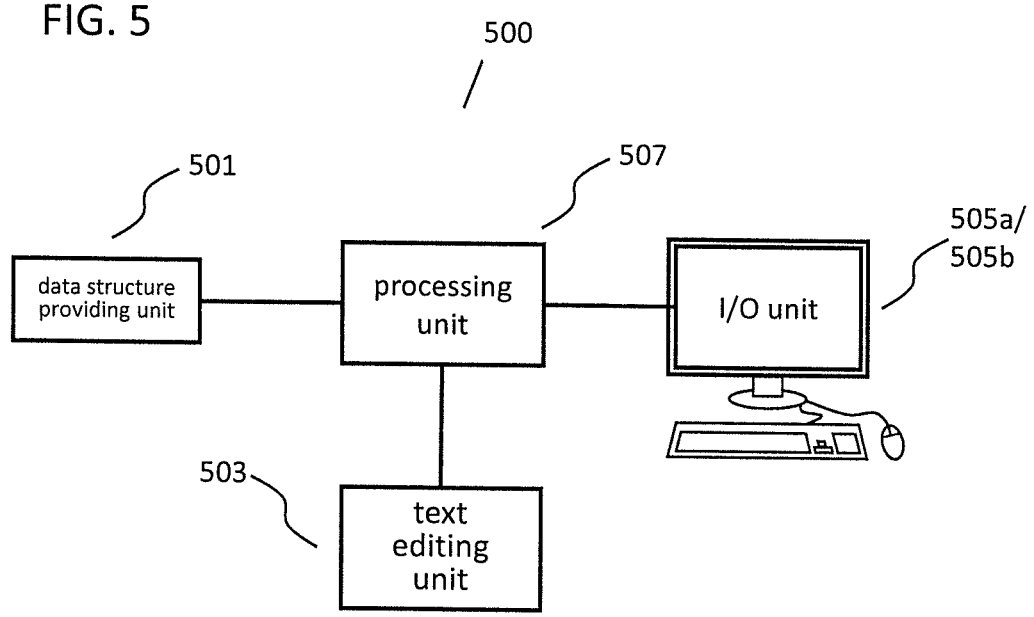
FIG. 5 schematic illustration of a computer system according to the invention.

FIG. 5 illustrates such a system 500 comprising a data structure providing unit 501, a text editing unit 503 and a processing unit 507.

In some embodiments, system further comprises an output unit 505a configured to display a data structure interface and, if required, also the text editing interface, and an input unit 505b configured to record user input. The processing unit 507 can further be configured to control the output unit and the input unit and to carry out any of the method steps described above.

The processing unit 507 can, e.g., consist of a single- or multicore processor or multiple physical processors (also referred to as multiple sockets).

According to another aspect of the invention, a computer program product for creating structured medical findings reports is provided, which is stored on a non-volatile storage medium and contains computer-readable instructions for carrying out any of the method steps described above.

Using the aspects and embodiments of this invention, the established efficient way of working with medical findings (working with free text via keyboard input or dictation) is maintained and at the same time medical findings are structured and recorded in a data structure.

Medical data becomes machine-readable due to the structured acquisition and can be used directly for analytical purposes. This makes the data digitally available to other IT applications (e.g., controlling, artificial intelligence, etc.). Thus, important expert information is not lost because it is free text. In addition, there is the possibility of encoding the data. The coding can be done according to medical ontologies such as SNOWMED, ICD-10, etc. and thus link the database entries with unique meaningful relationships. In another example the data is encoded according to billing codes to enable an efficient and optimized cost recording.

What is claimed is:

1. A computer-implemented method for creating structured medical findings reports comprising:
    a) providing a hierarchically organized and dynamically adaptable data structure comprising at least one data structure element;
    b) providing a text editing interface for creating and displaying a report text consisting of user-entered free text and/or structured text stored in the data structure elements and transferred into the report text;
    c) identifying, in the report text, first report text elements that are assignable to at least one data structure element and second report text elements that are not assignable to any of the existing data structure elements;
    d) assigning the first report text elements to the at least one data structure element, to which they are assignable;
    e) creating one or more new data structure elements and assigning and storing second report text elements to the one or more new data structure elements in such a way that the order of the report text is maintained; and f) assigning and storing second report text elements to existing data structure elements in such a way that the order of the report text created in the text editing interface is maintained.

2. The method according to claim 1, further comprising providing a data structure interface providing graphical representation and interaction with the data structure elements.

3. The method according to claim 2, in which text associated with data structure elements is transferred to the report text by interacting with the text associated with data structure element via the data structure interface.

4. The method according to claim 1, in which second report text elements which immediately follow a first text element are assigned to the data structure element to which the first report text element is assignable, and in which, in step e), the one or more newly created data structure elements are inserted into the data structure at the same or a subordinate hierarchy level as the data structure element to which the first report text element is assignable.

5. The method according to claim 1, in which second report text elements which, in the report text, immediately follow a first text element are in step f) assigned and stored to the data structure element to which the first text element is assignable.

6. The method according to claim 1, further comprising making text input suggestions for report text elements contained in the data structure elements and transferable to the report text.

7. The method according to claim 6, in which the proposed report text elements are contained in data structure elements at the hierarchy level associated with the currently processed section of the report text.

8. The method according to claim 6, in which the suggested report text elements are contained in data structure elements that have been used in findings reports of previous, similar cases of other patients, or in previous findings reports of the same patient.

9. The method according to claim 1, in which a report text element is identified as the first report text element if automatic text recognition determines that said report text element matches a text element stored in at least one data structure element within a predetermined linguistic similarity range.

10. The method according to claim 9, further comprising suggesting to a user to assign the identified first text element to the at least one data structure element in which a matching text element is stored.

11. The method according to claim 9, in which, further comprising suggesting to a user to use the at least one data structure element in which a matching text element is stored for creating the report text.

12. The method according to claim 1, further comprising allowing a user to define new data structure elements or text elements, which are associated there with and are transferable to the report text.

13. A computer system for creating structured medical findings reports, comprising:
 a data structure providing unit configured to provide and store hierarchically organized and dynamically adaptable data structures comprising at least one data structure element;
 a text editing unit configured to provide a text editing interface for creating and displaying a report text consisting of user-entered free text or structured text stored in the data structure elements and transferred into the report text;
 a processing unit configured to control the data structure providing unit and the text editing unit, wherein the processing unit is configured to:
  a) identify, in the report text, first report text elements contained in the report text that are assignable to at least one data structure element and second report text elements that are not assignable to any of the existing data structure elements;
  b) assign in the data structure providing unit the first report text elements to the at least one data structure element, to which they are assignable;
  c) create in the data structure providing unit one or more new data structure elements and to assign and store in the data structure providing unit second report text elements to them in such a way that the order of the report text is maintained; and
  d) assign and store in the data structure providing unit second report text elements to existing data structure elements in such a way that the order of the report text created in the text editing interface is maintained.

14. The computer system according to claim 13, comprising
 an output unit configured to display a data structure interface, and
 an input unit configured to record user input.

15. A computer program product for creating structured medical findings reports which is stored on a non-volatile storage medium and contains computer-readable instructions for carrying out the steps of a method comprising:
 a) providing a hierarchically organized and dynamically adaptable data structure comprising at least one data structure element;
 b) providing a text editing interface for creating and displaying a report text consisting of user-entered free text or structured text stored in the data structure elements and transferred into the report text;
 c) identifying, in the report text, first report text elements that are assignable to at least one data structure element and second report text elements that are not assignable to any of the existing data structure elements;
 d) assigning the first report text elements to the at least one data structure element, to which they are assignable;
 e) creating one or more new data structure elements and assigning and storing second report text elements to the one or more new data structure elements in such a way that the order of the report text is maintained; and
 f) assigning and storing second report text elements to existing data structure elements in such a way that the order of the report text created in the text editing interface is maintained.

16. The computer program product of claim 15, wherein the method further comprises providing a data structure interface providing graphical representation and interaction with the data structure elements.

17. The computer program product of claim 16, in which text associated with data structure elements is transferred to the report text by interacting with the text associated with data structure element via the data structure interface.

18. The computer program product of claim 15, in which second report text elements which immediately follow a first text element are assigned to the data structure element to which the first report text element is assignable, and in which, in step e), the one or more newly created data structure elements are inserted into the data structure at the same or a subordinate hierarchy level as the data structure element to which the first report text element is assignable.

19. The computer program product of claim 15, in which second report text elements which, in the report text, immediately follow a first text element are in step f) assigned and stored to the data structure element to which the first text element is assignable.

20. The computer program product of claim 15, further comprising making text input suggestions for report text elements contained in the data structure elements and transferable to the report text.

\* \* \* \* \*